(12) United States Patent
Christensen et al.

(10) Patent No.: US 8,026,106 B1
(45) Date of Patent: Sep. 27, 2011

(54) REMOVAL OF MERCURIC CHLORIDE CRYSTALS FROM FIXED TISSUES

(75) Inventors: Kimberly Christensen, Tucson, AZ (US); Annie Pomerantz, Oracle, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1772 days.

(21) Appl. No.: 11/013,136

(22) Filed: Dec. 15, 2004

Related U.S. Application Data (60) Provisional application No. 60/530,686, filed on Dec. 18, 2003.

(51) Int. Cl.
*G01N 1/28* (2006.01)
(52) U.S. Cl. .......................................... 436/175; 436/63
(58) Field of Classification Search .................. 436/139, 436/174–177, 63
See application file for complete search history.

(56) References Cited

U.S. PATENT DOCUMENTS

| | | | | |
|---|---|---|---|---|
| 2,393,580 | A * | 1/1946 | Weiskopf | 435/40.52 |
| 5,244,787 | A * | 9/1993 | Key et al. | 435/7.9 |
| 5,595,707 | A | 1/1997 | Copeland et al. | 422/64 |
| 5,672,696 | A * | 9/1997 | Wang et al. | 536/25.42 |
| 5,875,286 | A | 2/1999 | Bernstein et al. | 395/82 |
| 6,045,759 | A | 4/2000 | Ford et al. | 422/103 |
| 6,296,809 | B1 | 10/2001 | Richards et al. | 422/64 |
| 6,352,861 | B1 | 3/2002 | Copeland et al. | 436/46 |
| 6,544,798 | B1 | 4/2003 | Christensen et al. | 436/177 |
| 6,632,598 | B1 * | 10/2003 | Zhang et al. | 435/4 |

FOREIGN PATENT DOCUMENTS

| | | |
|---|---|---|
| EP | 0 600 939 | 10/1999 |
| WO | WO02/42737 | * 5/2002 |

OTHER PUBLICATIONS

O'Leary et al, Histochemical Journal vol. 26, 337-346 (1994).*
http://www.thefreedictionary.com/aqueous.*

* cited by examiner

*Primary Examiner* — Jan Ludlow (57) ABSTRACT

Mercuric chloride precipitates are removed from biological cell samples fixed with mercuric chloride and held in an embedding media, by contacting the biological cell samples with an aqueous solution containing a surfactant, and incubating at a temperature in excess of about 50° C. for a period of time.

10 Claims, 9 Drawing Sheets

REMOVAL OF MERCURIC CHLORIDE CRYSTALS FROM FIXED TISSUES

CROSS REFERENCE TO RELATED APPLICATION

This application claims priority from U.S. Provisional Application Ser. No. 60/530,686, filed Dec. 18, 2003.

BACKGROUND OF THE INVENTION

1. Field of the Invention

This invention relates to methods and apparatus useful in analysis or testing of tissue samples.

2. Description of Related Art

The analysis of tissue is a valuable diagnostic tool used by pathologists to diagnose many illnesses and by medical researchers to obtain information about a cell structure.

In order to obtain information from a tissue sample usually it is necessary to perform a number of preliminary operations to prepare the sample for analysis. There are many variations of the procedures to prepare tissue samples for testing. These variations may be considered refinements to adapt the process for individual tissues or because a particular technique is better suited to identify a specific chemical substance or enzyme within the tissue sample. However the basic preparation techniques are essentially the same.

Typically such operations include processing of the tissue by fixation, dehydration, infiltration and embedding; mounting of the tissue on a slide and then staining the sample for analysis by a microscope.

Depending on the analysis or testing to be done, a sample may have to undergo a number of preliminary steps or treatments or procedures before it is ready to be analyzed for its informational content. Typically the procedures are complex and time consuming, involving many tightly sequenced steps often utilizing expensive and/or toxic materials.

These procedures usually must be performed in a critical order for each sample and each treatment often is time dependent. Additionally the laboratory often is under extreme pressure to perform many different analysis as soon as possible, entailing many different procedures and tests.

For example, a tissue sample may undergo an optical microscopic examination so that the relationship of various cells to each other may be determined or abnormalities may be uncovered. The tissue sample typically is an extremely thin strip of tissue so that light may be transmitted therethrough. The average thickness of the tissue sample or slice (often referred to as a section) is on the order of 2 to 8 microns. A relatively soft and pliable tissue such as might come from an organ of the human body, in its fresh state cannot be accurately cut into such thin sections. In addition, in order to see individual elements of the cells, such as the nucleus, the nucleolus, the cytoplasm and the cell membrane, it is preferable to color or stain them by different dyes to produce a contrasting appearance between the elements. Very limited dye staining can be done on fresh or recently living tissue without resorting to chemical processing. Typically a sample of tissue 2.0 to 2.5 square centimeters in area and 3 to 4 millimeters thick is utilized. The tissue sample is then fixed in a material (a fixative), which serves to preserve the cellular structure but also to stop further enzymic action, which could result in the putrification or autolysis of the tissue.

To prepare good samples for microscopic examination the initial step should kill the enzymic processes of the tissue and should alter or denature the proteins of the cell through fixation. The period of fixation may take several hours or even a few days depending upon the tissue type, sample size and type of fixative being used. After fixation, the tissue sample often is dehydrated by the removal of water from the sample through the use of increasing strengths of alcohol or of some other dehydrating fluid. Gradual dehydration is preferred because it causes less distortion to the sample than a rapid dehydration process.

The alcohol or dehydrating fluid is then replaced by a chemical, which can permeate the tissue sample and give it a consistency suitable for the preparation of thin sections without disintegration or splitting. Fat solvents, such as chloroform or toluene commonly are used for this step. The sample, which has been dehydrated by the infiltration of alcohol, is next exposed to several changes of solvent over a period that may last from a few hours to days until the alcohol is completely replaced by the solvent. The sample is then exposed to a molten wax. After the wax infiltration the sample is allowed to cool and the wax solidify so that the sample is entirely embedded in and infiltrated by the wax.

A microtome is then utilized to cut thin slices from the tissue sample. The slices are on the order of 5 to 6 microns thick. The cut thin sections are floated on water to spread or flatten the section. The section is then disposed on a glass slide, usually measuring about 8 by 2.5 millimeters.

The wax is then removed by exposing the sample to a solvent, the solvent removed by alcohol, and the alcohol removed by decreasing the alcoholic concentrations until eventually the tissue is once more infiltrated by water. The infiltration of the sample by water permits the staining of the cell constituents by water-soluble dyes.

Prior to the development of automated procedures for the preparation of tissue samples, it often took from 2 to 10 days for manual processing before a tissue could be examined under a microscope. In more recent years automated processes have been developed utilizing apparatus to transfer the sample from one fluid to another at defined intervals, and as a result tissue sample preparation time has been significantly reduced to between about 4 and 16 hours. Such automated apparatus are described in the patent literature (see for example Copeland et al. U.S. Pat. No. 5,595,707, Richards et al. U.S. Pat. No. 6,296,809 and Copeland et al. U.S. Pat. No. 6,352,861), and are available commercially such as the Benchmark® automated slide processor and the Discovery™ automated slide processor both available from Ventana Medical Systems, Inc. of Tucson, Ariz.

While automated slide processors have become widely adopted, heretofore automated processors could not be used when processing slides fixed with mercuric chloride ($HgCl_2$) without taking the slides off-line to remove mercurous chloride precipitates.

Figure 1:
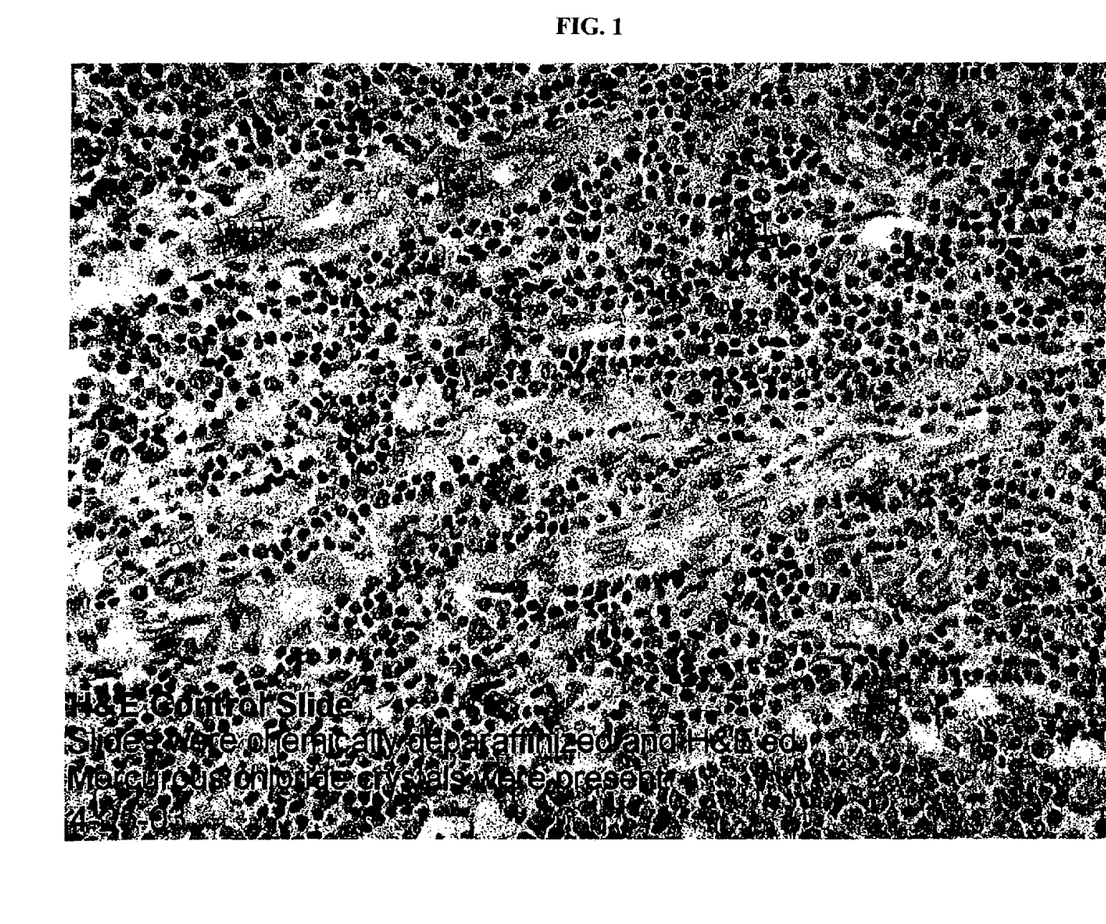
FIGS. 1 and 2 are standard mercuric chloride fixed H and E stained slides before and after processing to remove mercurous chloride precipitates according to the prior art.

Mercuric chloride is one of the more common and preferred fixatives. Mercuric chloride is a powerful protein precipitant and forms intermolecular mercury links between S—H carboxyl and amino groups. It penetrates reasonably well, shrinks tissue less than many other common protein coagulants, hardens tissue moderately, and distorts the cells less than many other common fixatives and thus is preferred in many applications. Notwithstanding the foregoing, a primary disadvantage to the use of mercuric chloride based fixatives is the formation of precipitates on the tissue section. The precipitates, which are formed as crystalline granules, comprise mercurous chloride (HgCl), which are highly conspicuous and interfere with reading of a stain at the microscopic level. (See FIG. 1).

While slides fixed with other fixatives, such as formaldehyde, formalin, picric acid, etc., have been successfully processed on automated systems as above described, for slides fixed with mercuric chloride, two additional manual steps are required in order to remove the mercurous chloride precipitates as follows:

(1) The slides first are placed into an aqueous solution that contains iodine. This step converts the mercurous chloride precipitates to water soluble mercuric chloride, and mercuric iodine according to the reaction:

$$2HgCl + I_2 = HgCl_2 + HgI_2$$

(2) The slides are then rinsed and placed in an aqueous solution containing sodium thiosulfate to convert any free iodide to water soluble sodium iodide according to the reaction:

$$2NA_2S_2O_3 + I_2 = 2NaI + Na_2S_4O_6$$

Figure 2:
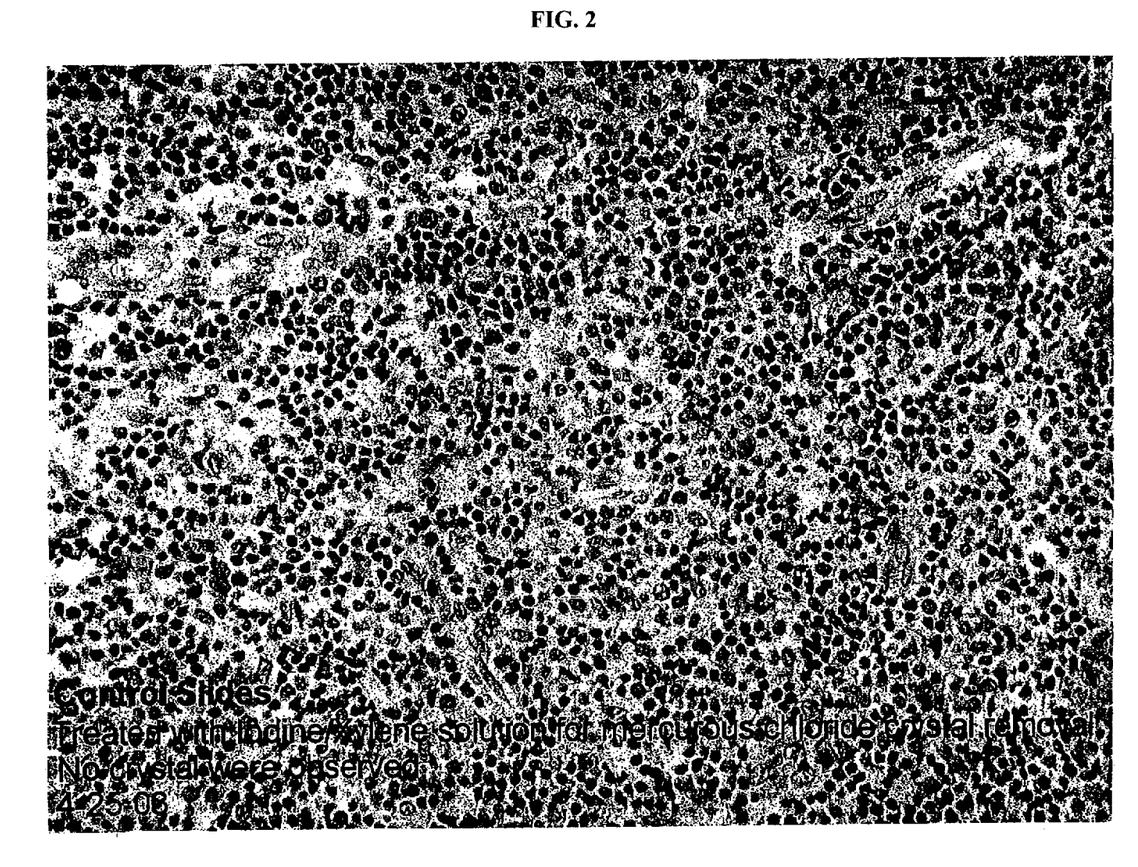

While these added process steps remove the mercurous chloride precipitates (see FIG. 2), these two added process steps, which typically are run off line, add significant costs and delays.

SUMMARY OF THE INVENTION

The present invention provides a system for removal of mercurous chloride precipitates from slides fixed with mercuric chloride contemporaneously with the deparaffinization step or cell conditioning step by subjecting the slides to a wash or soak with hot water containing a surfactant.

One embodiment of the present invention involves exposing mercuric chloride fixed biological samples to selected fluids so as contemporaneously to remove mercurous chloride precipitates and the embedding materials in which the biological samples have been embedded for preservation and support. In one embodiment of the present invention, the embedding material comprises paraffin, and the mercurous chloride precipitates and paraffin are removed from mercuric chloride fixed biological samples by washing the slides with hot water containing a surfactant.

In a preferred method of the present invention, a paraffin-embedded mercuric chloride fixed biological sample carried on the glass slide is first heated by a heating element of an automated staining instrument, such as on a thermal platform as disclosed in U.S. Pat. No. 6,296,809 and U.S. Pat. No. 6,544,798, within an automated staining instrument such as disclosed in U.S. Pat. No. 6,045,759 all of which are herein incorporated by reference, such that the sample slide is dried and the paraffin is melted. The heating element exposes heat to one side of the biological sample. The slides are then washed or rinsed with hot water containing a surfactant. The hot water rinse removes not only the embedding medium, but also removes mercurous chloride precipitates from the tissue sample. The removal of the mercurous chloride precipitates from the sample by washing or rinsing with water is unexpected since mercurous chloride is considered to be essentially insoluble in water.

In another embodiment of the invention, the cells are conditioned following deparaffinization by a soak with hot water containing a buffering agent such as tris buffers, citrate buffers, or phosphate buffers as found in commercially available products such as Reaction Buffer Solution, Sodium Chloride Sodium Citrate Wash Solution (2×SSC), Cell Conditioning 1 Solution (CC1) or Cell Conditioning 2 Solution (CC2) all available from Ventana Medical Systems, Inc. of Tucson, Ariz.

BRIEF DESCRIPTION OF THE DRAWINGS

Further features and advantages of the present invention will be seen from the following detailed description, taken in conjunction with the accompanying drawings, wherein.

DETAILED DESCRIPTION OF PREFERRED EMBODIMENTS

Figure 3:
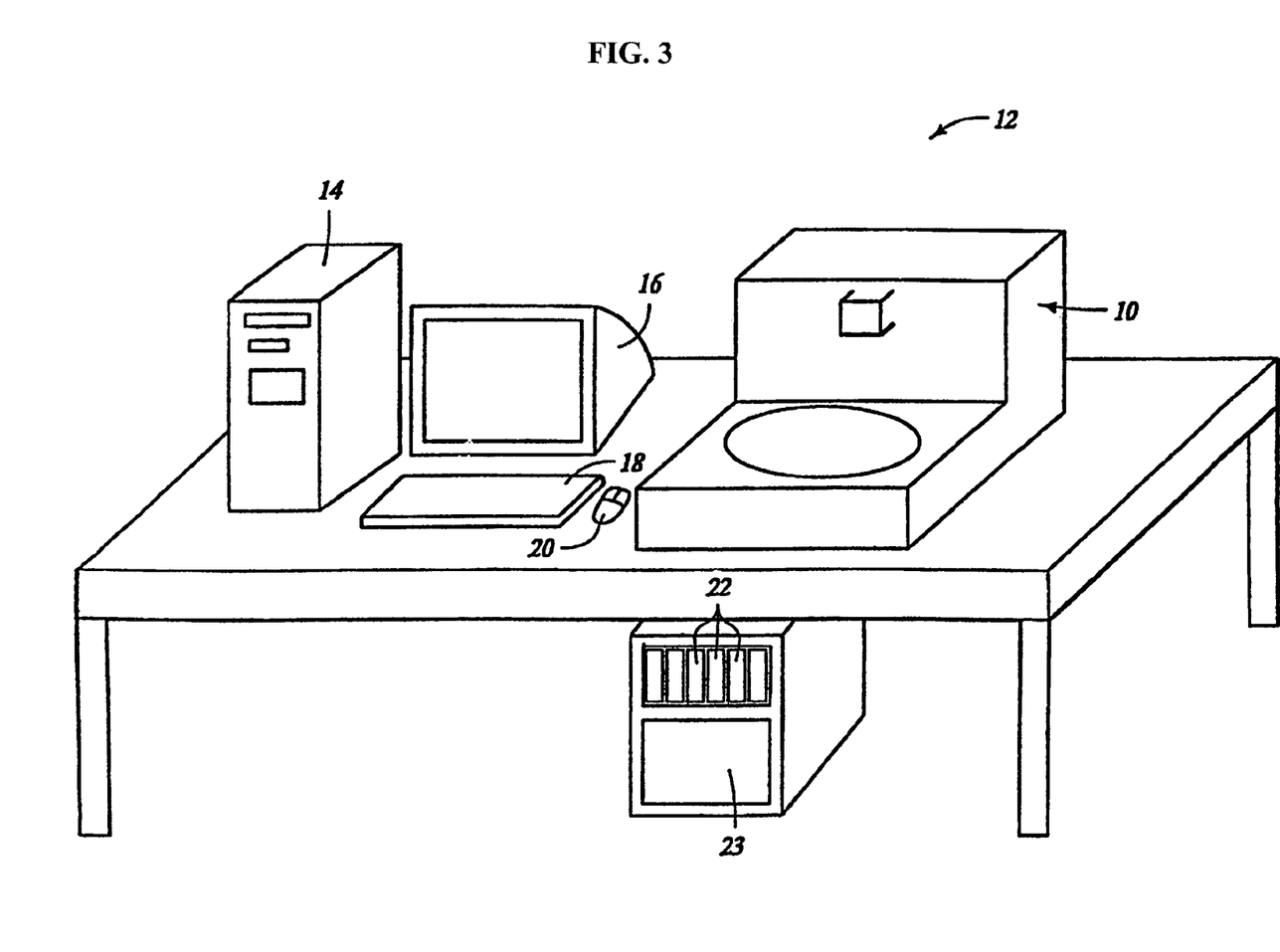
FIG. 3 is a perspective view of an apparatus useful for practice of the present invention shown in conjunction with a computer and other instruments with which it operates.

Referring now in detail to the drawings wherein like parts are designated by like reference numerals throughout, there is illustrated in FIG. 3 a perspective view of the molecular pathology apparatus according to the present invention which is designated generally by reference numeral 10. Apparatus 10 is designed to automatically stain or otherwise treat tissue mounted on microscope slides with nucleic acid probes, antibodies, and/or reagents associated therewith in the desired sequence, time and temperature.

In a preferred embodiment, apparatus 10 functions as one component or module of a system 12 which also comprises a host computer 14 preferably a personal computer, a monitor 16, keyboard 18, mouse 20, bulk fluid containers 22, waste container 23 and related equipment. Additional staining modules or other instruments may be added to system 12 to form a network with computer 14 functioning as a server. Alternatively, some or all of these separate components could be incorporated into apparatus 10 making it a stand-alone instrument.

The preferred configuration of apparatus 10 as well as system 12 is generally as described in U.S. Pat. No. 6,045,759 as well as in the Ventana NexES User's Guide available from Ventana Medical Systems, Inc. (Tucson, Ariz.), both incorporated herein. For purposes of clarity, detailed descriptions of those components found in both the present invention and the incorporated references are omitted.

In brief, apparatus 10 is a microprocessor controlled staining instrument that automatically applies chemical and biological reagents to tissue mounted on standard glass microscope slides. A carousel supporting radially positioned glass slides is rotated by a stepper motor to place each slide under one of a series of reagent dispensers. Apparatus 10 controls dispensing, washing, mixing, and heating to optimize reaction kinetics. The computer controlled automation permits use of apparatus 10 in a walk-away manner, i.e. with little manual labor.

Apparatus 10 comprises a housing formed of a lower section 30 removably mounted or hinged to an upper section 32. A slide carousel 34 is mounted within lower section 30 for rotation about axis A-A. As set forth in greater detail below, a plurality of thermal platforms 50 are mounted radially about the perimeter of carousel 34 upon which standard glass slides with tissue samples may be placed. Carousel 34 is preferably constructed of stainless steel. The temperature of each slide may be individually controlled by means of various sensors and microprocessors as described in U.S. Pat. No. 6,544,798. Also housed within apparatus 10 (FIG. 4) are wash dispense nozzles 36, Coverslip™. dispense nozzle 37, fluid knife 38, wash volume adjust nozzle 39, bar code reader mirror 40, and air vortex mixers 42 the details of which also are discussed in detail in U.S. Pat. No. 6,544,798, incorporated herein by reference.

Figure 4:
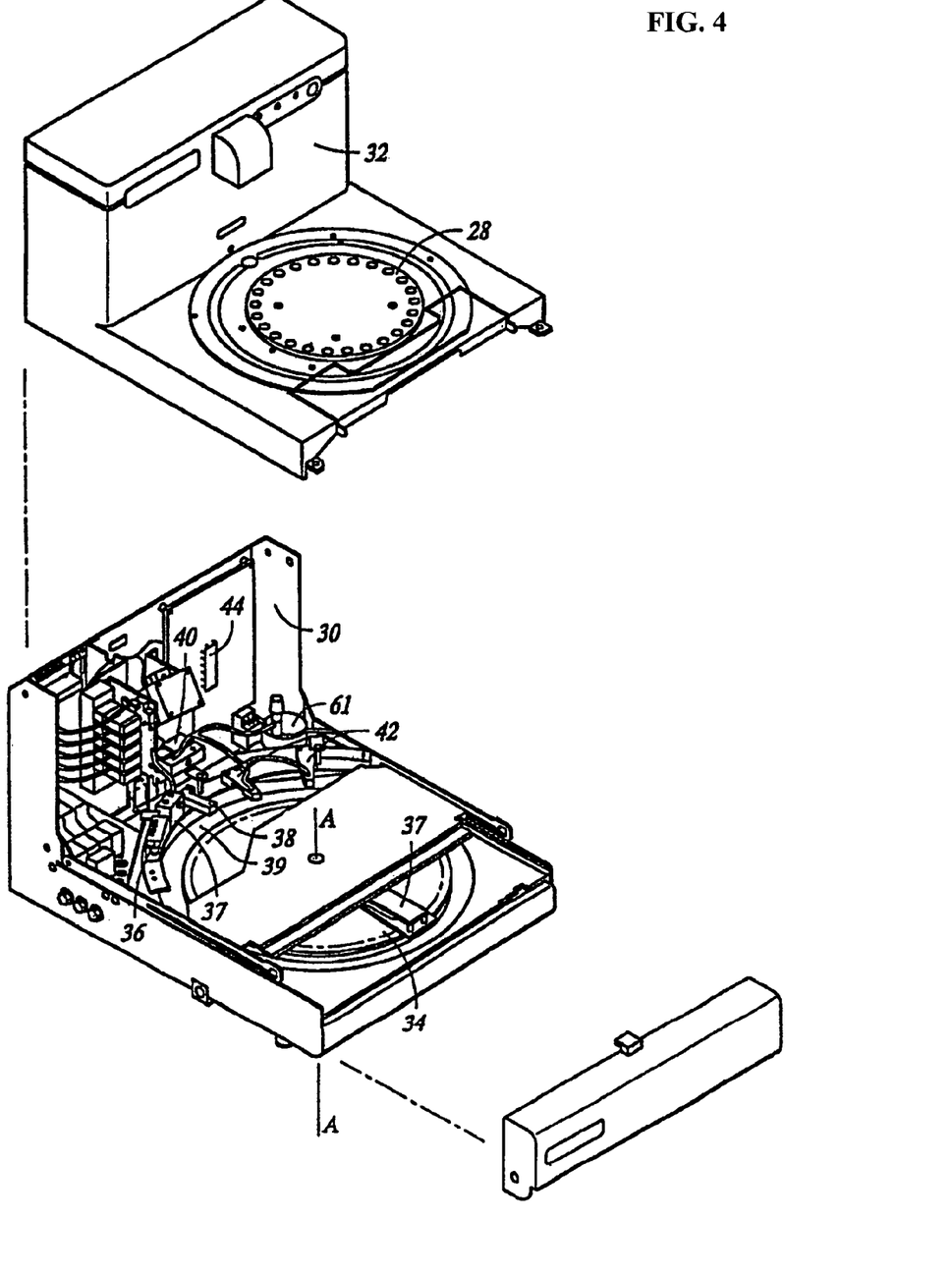
FIG. 4 is an exploded view of the apparatus of FIG. 3.

Rotatably mounted atop upper section 32 is a reagent carousel 28. Reagent dispensers (not shown) are removably mounted on a reagent tray (not shown), which in turn, is adapted to engage carousel 28, as, described in U.S. Pat. No. 6,544,798. Reagents may include any chemical or biological material conventionally applied to slides including nucleic acid probes or primers, polymerase, primary and secondary antibodies, digestion enzymes, pre-fixatives, post-fixatives, blocking agents, readout chemistry, and counterstains. Reagent dispensers preferably are bar code labeled for identification by the computer. For each slide, a single reagent is applied and then incubated for a precise period of time in a temperature-controlled environment. Mixing of the reagents is accomplished by compressed air jets aimed along the edge of the slide thus causing rotation of the reagent. After the appropriate incubation, the reagent is washed off the slide using nozzles 36. Then the remaining wash buffer volume is adjusted using the volume adjust nozzle 39. Liquid Coverslip™ solution, to inhibit evaporation, is then applied to the slide via nozzle 37. Air knife 38 divides the pool of Liquid Coverslip™ solution, followed by the application of the next reagent. These steps are repeated as the carousels turn until the protocol is completed.

In addition to host computer 14, apparatus 10 preferably includes its own microprocessor 44 to which information from host computer 14 is downloaded. In particular, the computer downloads to microprocessor 44 both the sequence of steps in a run program and the sensor monitoring and control logic called the "run rules" as well as the temperature parameters of the protocol. Model No. DS2251T 128K from Dallas Semiconductor, Dallas Tex. is an example of a microprocessor that can perform this function.

A feature and advantage of the present invention resides in the discovery that mercurous chloride precipitates, normally considered to be essentially insoluble in water, can be removed from a mercuric chloride fixed biological sample contemporaneously with the deparaffinization step by subjecting the slides to a wash with hot water containing a surfactant. Typically, the biological sample is placed on the top surface of a slide (such as a glass slide). The slide is then placed on top of a thermal platform or slide heater so that the bottom surface of the slide is in contact with the thermal platform. The thermal platform, via conduction, heats the bottom surface of the slide to a temperature above the melting point of paraffin, which typically melts at between about 50-57° C. After heating the slide, the slide is then subjected to one or more wash, soak and/or rinse cycles using hot water containing a surfactant.

The water should be heated to a temperature above the melting point temperature of the paraffin. Typically, the water is heated to a temperature of about 50-100° C., more preferably about 55-85° C.

Preferably the water comprises deionized water, and contains 3 to 30 volume percent of an ionic or non-ionic surfactant such as Triton X-100, Tween, Brij, saponin and sodium dodecylsulfate, or Colaterage LFD-C. The surfactant lowers the surface tension of the aqueous fluid, allowing the aqueous fluid to spread better over the surface of the slide. In one preferred embodiment of the invention, the aqueous fluid comprises EZ Prep™ which is available from Ventana Medical Systems, Inc. of Tucson, Ariz. EZ Prep™ is fluid comprising deionized water with about 3% by weight of a surfactant. It normally is diluted 10× for use. An additional ingredient may be added, acting as an anti-microbial agent, so that the fluid prior to application on the slide does not contain microbes. The use of heated water as a fluid to remove mercurous chloride precipitates during deparaffinization is quite different from the prior art which, as noted above used a two-step off-line process in which an aqueous solution of iodine is used to convert the water insoluble mercurous chloride to water soluble mercuric chloride, and an aqueous solution of sodium thiosulfate then used to remove any free iodine. As noted supra mercurous chloride is essentially insoluble in water. Moreover, water and paraffin are immiscible. Thus, the use of water to both remove a water immiscible paraffin embedding material and water insoluble mercurous chloride precipitate is unexpected.

The invention will be further described by reference to the following non-limiting Examples:

Example 1

Figure 5:
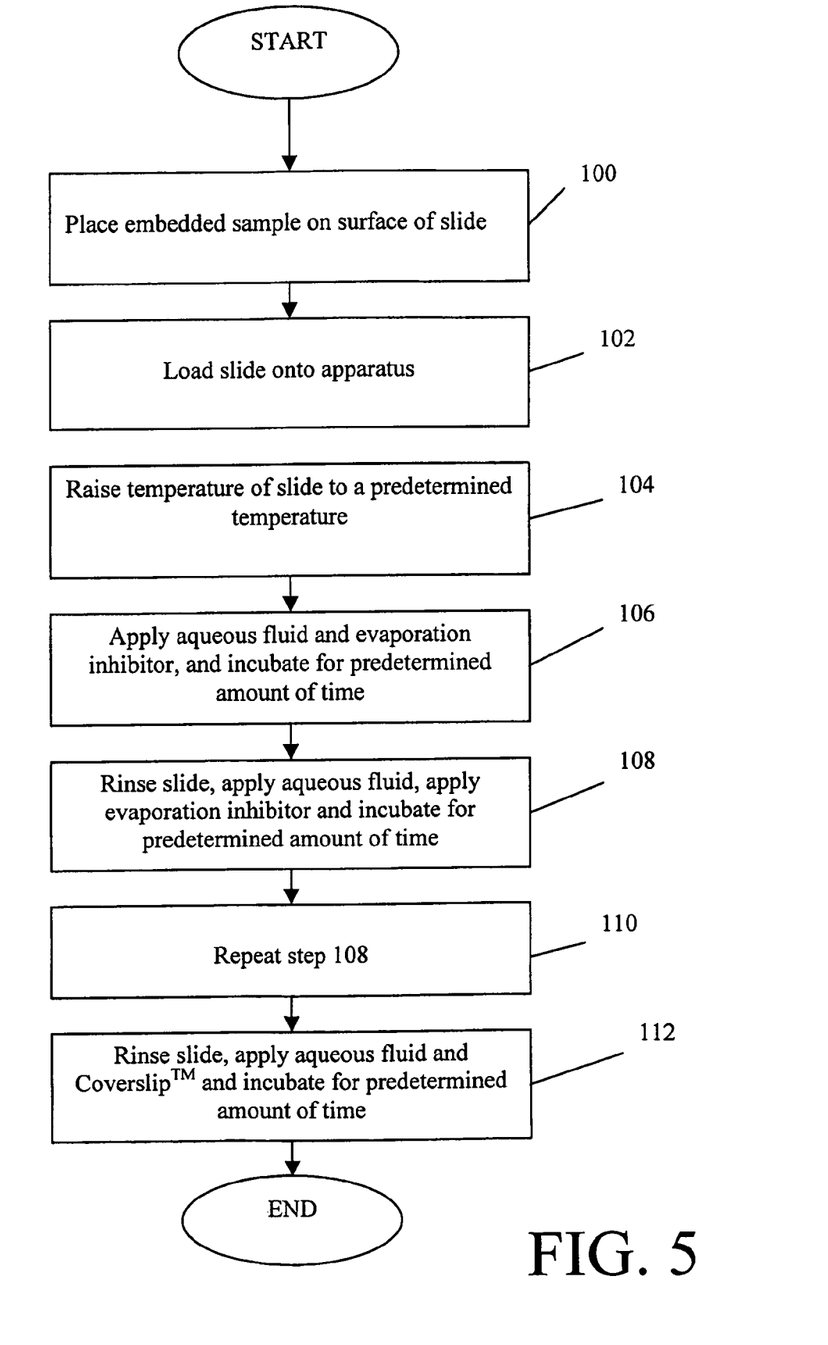
FIG. 5 is a flow chart for one embodiment for removing the embedding media and mercurous chloride precipitates from a slide in accordance with the present invention.

Referring to FIG. 5, the overall process is as follows:

A mercuric chloride fixed biological sample, embedded in paraffin wax is cut to 3-5 micron thick section and placed on a 1×3 inch glass specimen slide at step 100. The slide, is then loaded on a Benchmark® automated staining system available from Ventana Medical Systems, Inc. of Tucson, Ariz., at step 102.

The slides are then dry baked at 55-75° C. for 4-20 minutes at step 104.

The slides then are treated with a approximately 1.0 ml of EZ Prep™ and held (incubated) at 75° C. for 4 minutes at step 106.

The slides are then rinsed with 5-7 ml of deionized water containing EZ Prep™, and then treated with approximately 1.0 ml of EZ Prep™ as previously described, and held (incubated) at 75° C. for 4 minutes at step 108.

The slides are rinsed a second time with 5-7 ml of deionized water containing EZ Prep™, and are further treated with approximately 1.0 ml of EZ Prep™ as previously described and held (incubated) at 76° C. for 4 minutes at step 110.

The slides were then rinsed again with 5-7 ml of deionized water containing EZ Prep™. EZ Prep™ and Liquid Coverslip™ (LCS™) available from Ventana Medical Systems applied to the slides and the slides were incubated once more at 76° C. for 4 minutes at step 112.

Figure 8:
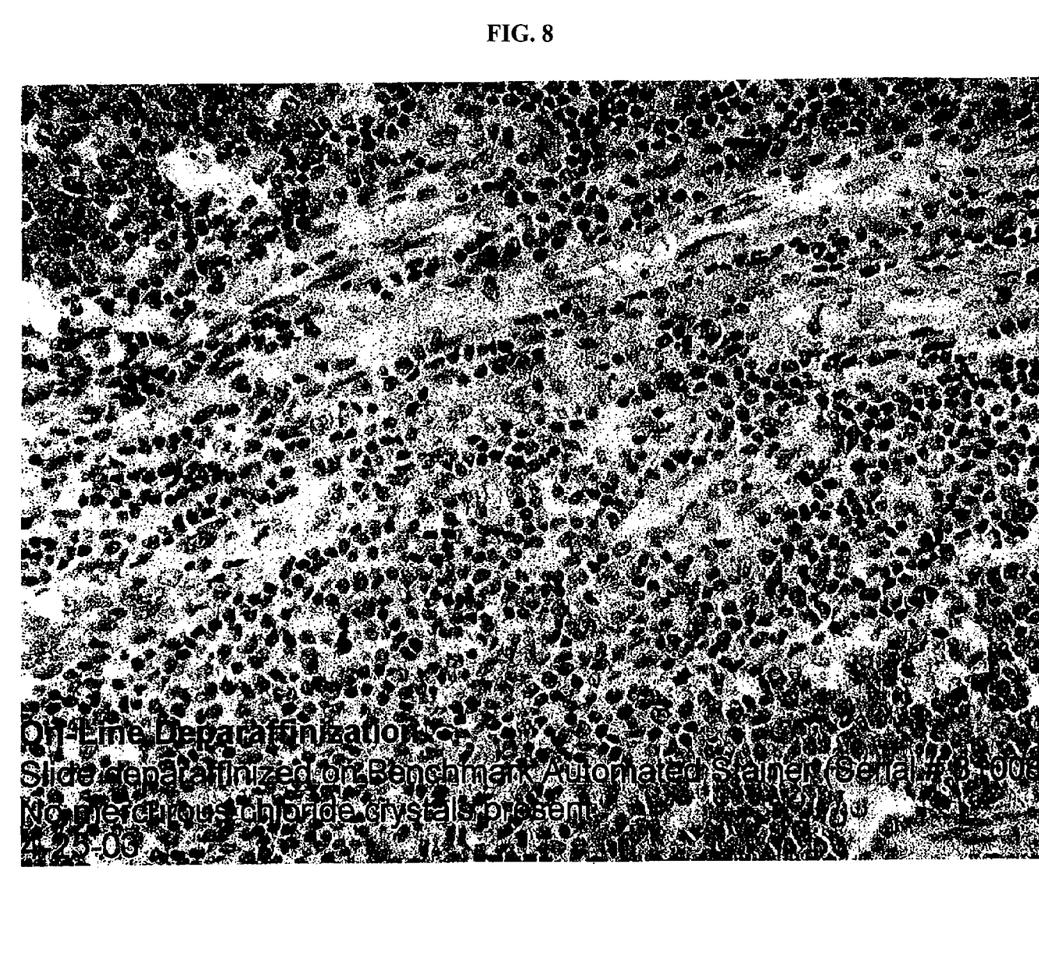

The slide was then stained and examined under a microscope and exhibited no mercurous chloride granules (FIG. 8).

Examples 2-4

The procedure of Example 1 was repeated using deionized water with a surfactant as previously described in steps 106, 108 and 110, under the following conditions. The slides were then examined for mercurous chloride granules and observations recorded as follows:

| Example | Treatment (incubation) Condition | Observation |
|---|---|---|
| Example 2 | 45° C. for 12 minutes | Marginal reduction of crystals |
| Example 3 | 55° C. for 12 minutes | No crystals observed |
| Example 4 | 65° C. for 12 minutes | No crystals observed |

Conclusion

For the decrystallization process to take place, the slides must be treated to an elevated temperature of at least 55° C.

The following Example 5 illustrates mercurous chloride crystal removal during a post-deparaffinization cell conditioning step.

Example 5

Figure 6:
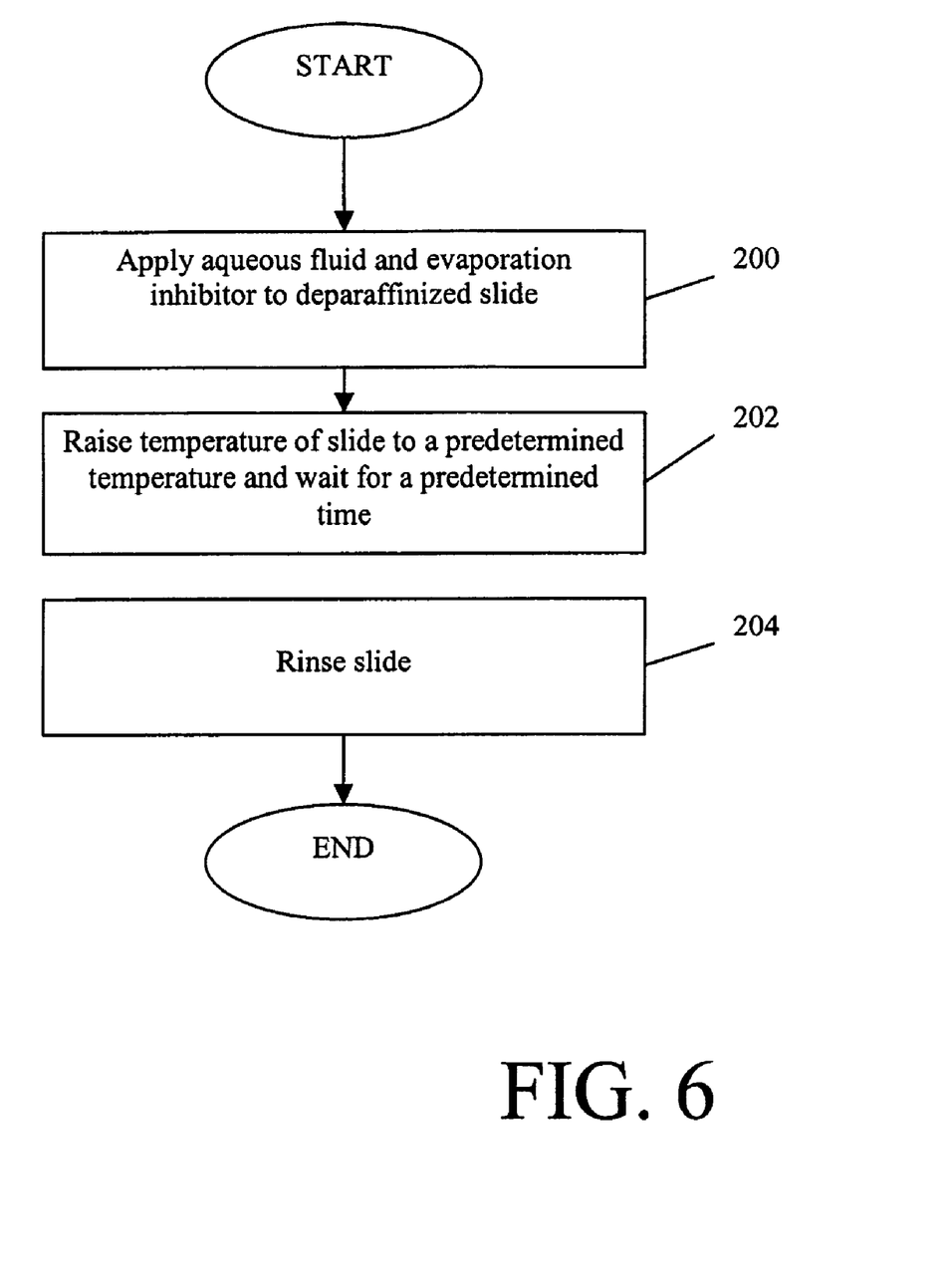
FIG. 6 is a flow chart for one embodiment for cell conditioning in accordance with the present invention.
Figure 7:
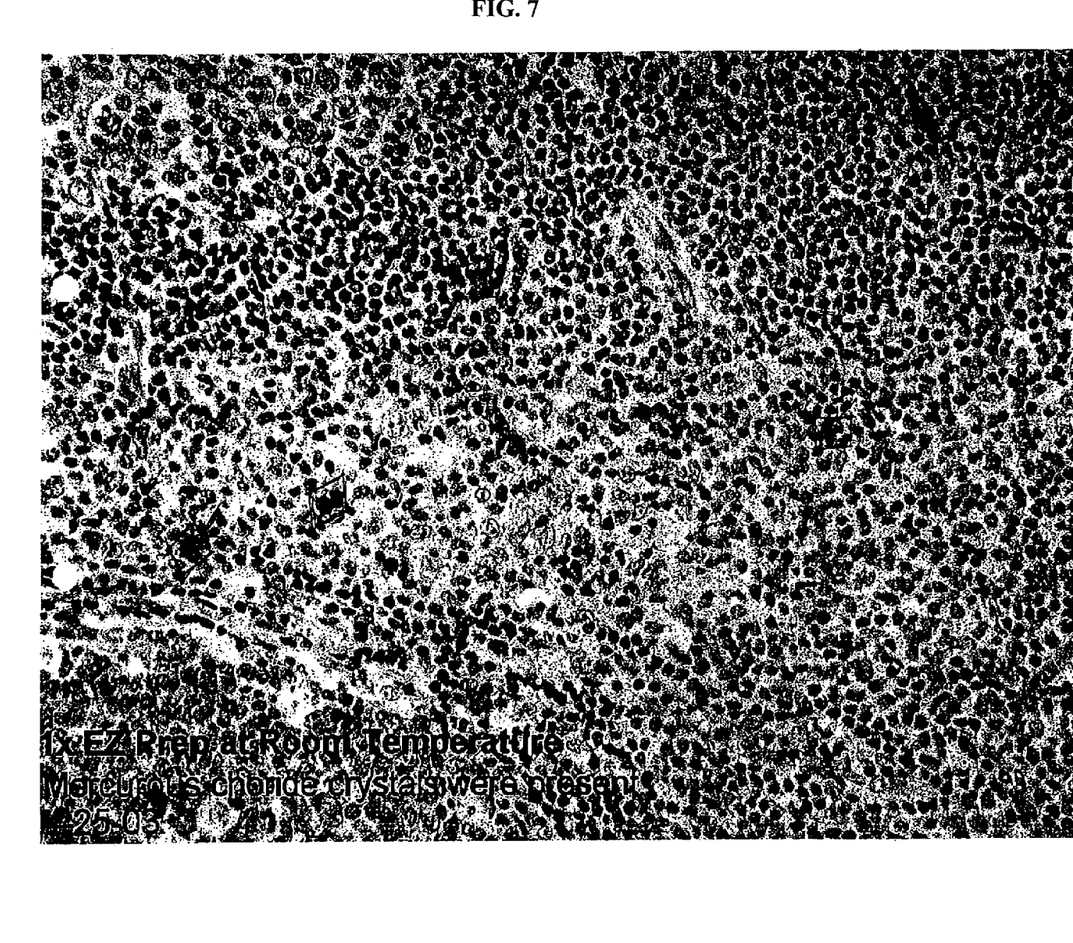
FIG. 7 is a control and FIGS. 8 and 9 are mercuric chloride fixed H and E stained slides processed in accordance with the present invention.
Figure 9:
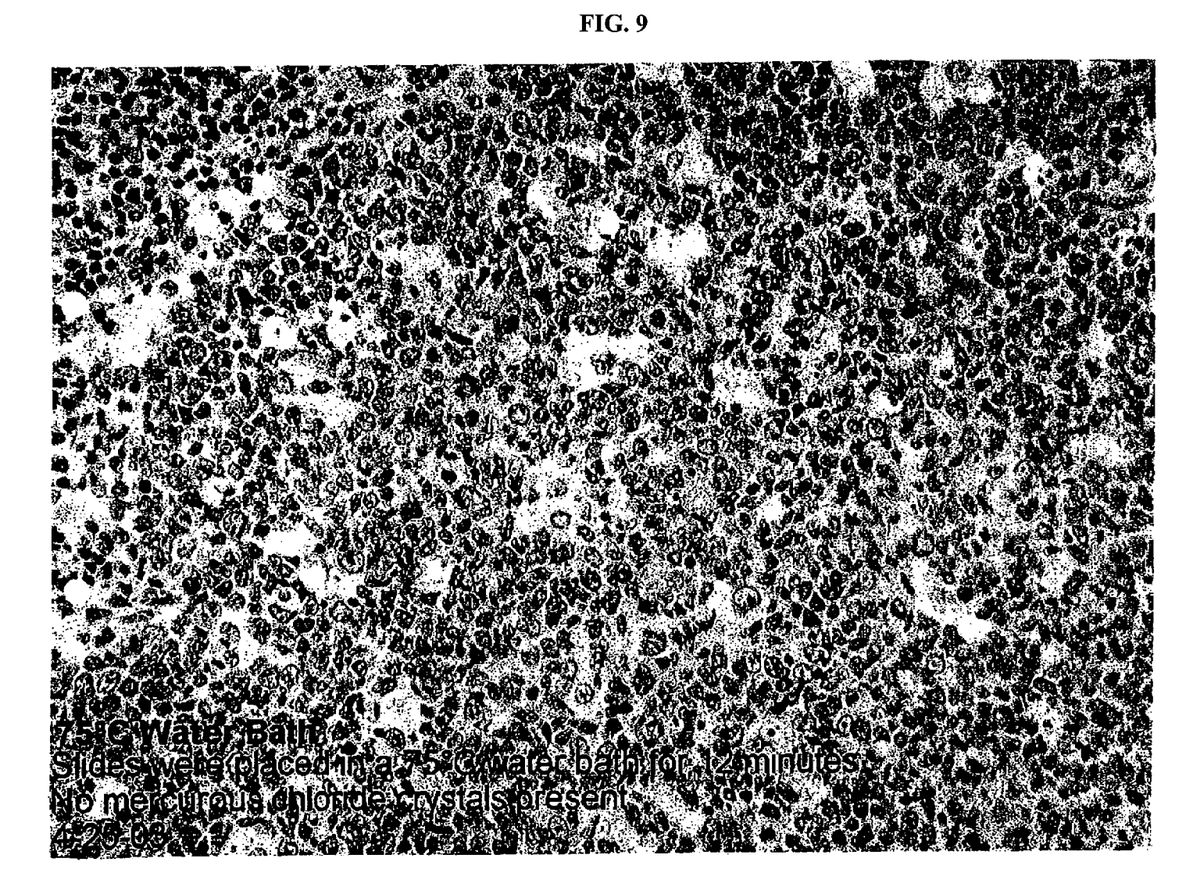

Referring to FIG. 6, conventionally processed slides, following deparaffinization, are subjected to cell conditioning using deionized water containing Cell Conditioning 1 Solution (CC1) at step 200. Slide temperature is raised to above about 95° C. and held at that temperature for times ranging from 8 minutes to 90 minutes under a film of Liquid Coverslip™ containing a mixture of polycarbon chains or a mixture of oils. Following conditioning, the cells are rinsed with deionized water, and examined under a microscope for mercurous chloride granules. No mercurous chloride granules were observed (see FIG. 9).

Various other reagents useful for cell conditioning include:
(a) 0.1M Tris/0.05% Brij and 0.05% Proclin;
(b) 0.01M Tris/0.001 MEDTA, 0.0075 M boric acid, 0.03% Brij and 0.05% Proclin;
(c) 0.01 M Citrate buffer, 0.3% sodium dodecylsulfate; 5% ethylene glycol and 0.05% Proclin; and
(d) 0.03 M Citrate Trisodium salt dehydrate, 0.3M NaCl, 0.05% Tritonx 100, and 0.05% Proclin.

Various changes and modifications may be made without departing from the true spirit and scope of the invention. This true spirit and scope of the invention is defined by the appended claims to be interpreted in light of the foregoing specification.

The invention claimed is:

1. A method of contemporaneously removing mercurous chloride precipitates and an embedding media from a biological cell sample, comprising:
providing a biological cell sample fixed with mercuric chloride and held in an embedding media;
contacting said biological cell sample with an aqueous solution containing a surfactant, at temperature in excess of about 50° C. thereby heating the embedding media sufficient to separate the embedding media from the biological cell sample; and
removing mercurous chloride precipitates and the embedding media contemporaneously from the biological cell sample by removing the aqueous solution containing a surfactant from the biological cell sample.

2. The method of claim 1, wherein the aqueous solution is preheated to a temperature in excess of about 55° C.

3. The method of claim 2, wherein the aqueous solution is preheated to a temperature in the range of 50-100° C.

4. The method of claim 1, wherein the sample is preheated to a temperature in excess of about 55° C.

5. The method of claim 4, wherein the sample is preheated to a temperature in the range of 55-85° C.

6. The method of claim 1, wherein the aqueous solution contains 3-30%, by volume of a surfactant.

7. The method of claim 6, wherein the surfactant comprises an ionic or a non-ionic material.

8. The method of claim 1, wherein the aqueous solution contains at least 70% of water by volume.

9. A method of removing mercurous chloride precipitates from a paraffin embedded mercuric chloride fixed biological cell sample following deparaffinization, wherein the biological sample is fixed on a slide, comprising:
contacting said deparaffinized biological cell sample on the slide with an aqueous based conditioning fluid containing a surfactant at a temperature in excess of about 85° C. for 8 to 90 minutes; and
removing the aqueous based conditioning fluid containing a surfactant from the biological cell sample on the slide, thereby removing the mercurous chloride precipitates.

10. The method of claim 9, wherein the aqueous based conditioning fluid is heated to a temperature in excess of about 95° C.

* * * * *